(12) United States Patent
Danzi et al.

(10) Patent No.: US 12,053,479 B2
(45) Date of Patent: Aug. 6, 2024

(54) TRANSDERMAL TREATMENT FOR ERECTILE DYSFUNCTION

(71) Applicant: Madera Pharmaceuticals, Inc., Las Vegas, NV (US)

(72) Inventors: Michael Danzi, Summerlin, NV (US); Charles Evans, Godalming (GB); Orla McCabe, Billingshurst (GB)

(73) Assignee: Madera Pharm aceuticals, Inc., Las Vegas, CA (US)

( * ) Notice: Subject to any disclaimer, the term of this patent is extended or adjusted under 35 U.S.C. 154(b) by 0 days.

(21) Appl. No.: 17/508,951

(22) Filed: Oct. 22, 2021

(65) Prior Publication Data

US 2022/0125802 A1    Apr. 28, 2022

Related U.S. Application Data

(60) Provisional application No. 63/104,158, filed on Oct. 22, 2020.

(51) Int. Cl.
| | |
|---|---|
| *A61K 31/5575* | (2006.01) |
| *A61K 9/00* | (2006.01) |
| *A61K 9/08* | (2006.01) |
| *A61K 31/417* | (2006.01) |
| *A61K 31/472* | (2006.01) |
| *A61K 47/10* | (2017.01) |
| *A61P 15/10* | (2006.01) |

(52) U.S. Cl.
CPC ........ *A61K 31/5575* (2013.01); *A61K 9/0014* (2013.01); *A61K 9/08* (2013.01); *A61K 31/417* (2013.01); *A61K 31/472* (2013.01); *A61K 47/10* (2013.01); *A61P 15/10* (2018.01)

(58) Field of Classification Search
CPC ... A61K 31/5575; A61K 9/0014; A61K 47/10
See application file for complete search history.

(56) References Cited

U.S. PATENT DOCUMENTS

| | | |
|---|---|---|
| 5,942,545 A | 8/1999 | Samour et al. |
| 2002/0151537 A1 | 10/2002 | Easterling |
| 2004/0102475 A1 | 5/2004 | Podolski |
| 2005/0283110 A1 | 12/2005 | Atala et al. |
| 2007/0167418 A1 | 7/2007 | Ferguson |
| 2007/0243216 A1 | 10/2007 | Kepka et al. |
| 2008/0004310 A1 | 1/2008 | Kelley, II et al. |
| 2008/0102089 A1 | 5/2008 | Cappello |
| 2009/0069359 A1 | 3/2009 | Cappello |
| 2009/0257956 A1 | 10/2009 | Sallis et al. |

(Continued)

FOREIGN PATENT DOCUMENTS

WO    WO-9965303 A1 * 12/1999    ............. A61K 47/10

OTHER PUBLICATIONS

Handbook of Pharmaceutical Excipients, 6th Ed, 2009, pp. 64-66, 283-286, and 592-594 (Year: 2009).*

(Continued)

*Primary Examiner* — San Ming R Hui
(74) *Attorney, Agent, or Firm* — FisherBroyles, LLC; Glen L Nuttall (57) ABSTRACT

A transdermal treatment for erectile dysfunction includes an aqueous solution having a plurality of excipients and a combination of papaverine, phentolamine mesylate and prostaglandin E1.

10 Claims, 5 Drawing Sheets

(56) References Cited

U.S. PATENT DOCUMENTS

| | | |
|---|---|---|
| 2014/0105963 A1 | 4/2014 | Perricone et al. |
| 2016/0317552 A1 | 11/2016 | Baum et al. |
| 2017/0326063 A1 | 11/2017 | Perricone |
| 2019/0021897 A1 | 1/2019 | Lange, IV |
| 2019/0282591 A1 | 9/2019 | Hanna et al. |

OTHER PUBLICATIONS

Wen, et al., Systemic Enhancement of Papaverine Transdermal Gel for Erectile Dysfunction, Drug Development and Industrial Pharmacy, 2012, pp. 912-922.

Chiang, et al., Papaverine and Prostaglandin E1 Gel Applications for Impotence, Annals of the Academy of Medicine Singapore, 1995, pp. 767-769.

Schultheiss, et al., Pharmacological Therapy in Erectile Dysfunction - Current Standards and New Viewpoint, https://pubmed.nobl.nim.nih.gov/9190765/, 1997.

Porst, H., Prostaglandin E1 in Erectile Dysfunction, https://pubmed.ncbi.nim.nih.gov/2655258, Mar. 1989.

Kursh, et al., Injection Therapy for Impotence, ://pubme gov/3055615/ Nov. 1988.

Usta, et al., Feline Penile Erection Induced By Topical Glans Penis Application Ofcombination Alprostadil and Sepa (Topiglan), https://pubmed.nobl.nim.nih.gov/14963475/, Jun. 2004.

Meinhardi, et al., Prostaglandin E1 With Phentolamine for the Treatment of Erectile Dysfunction, https://pubmed.nobl.nim.nih.gov/8735187/, Mar. 1996.

Floth, A., Topical Therapy in Erectile Dysfunction, https://pubmed.nobl.nim.nih.gov/10746290/, 2000.

Trissel, et al., Long-Term Stability of Trimix: a Three-Drug Injection Used To Treat Erectile Dysfunction, https://pubmed.nobi.nim.nih.gov/23924676/, May-Jun. 2004.

Wespes, et al., Effect of Phentolamine On Venous Return in Human Erection, https://pubmed.nobl.nim.nih.gov/2920269/, Jan. 1989.

Delcour, et al., The Effect of Papaverine On Arterial and Venous Hemodynamics of Erection, https:/pubmed.ncbi.nim.nih.gov/3599210/, Jul. 1987.

Azadzoi, et al., Hemodynamics of Penile Erection: Iii. Measurement of Deep Intracavernosal and Subtunical Blood Flow and Oxygen Tension, https://pubmed.no ih.gov/7815637/, Feb. 1995.

Juenemann, et al., Hemodynamics of Papaverine - And Phentolamine - Induced Penile Erection, https://pubmed.nobl.nim.nih.gov/3712604/, Jul. 1986.

Vieillard, et al., Physicochemical Stability Study of a New Trimix Formulation Fortreatment of Erectile Dysfunction, Annales Pharmaceutiques Francaises, vol. 71, Issue 5, Sep. 2013, pp. 358-363.

Porst, et al., Sop Conservative (Medical and Mechanical) Treatment of Erectile Dysfunction, The Journal of Sexual Medicine, vol. 10, Issue 1, Jan. 1, 2013, pp. 130-171.

Jain, et al., ALPROSTADIL, https cbi. h.gov/books/NBK542217/, Apr. 28, 2020.

Khera, et al., Erectile Dysfunction, https://www.ncbi.nim.nih.gov/pmc/articles/PMC3217797/, Jun. 29, 2011.

Kim, et al., Topical Prostaglandin - E1 for the Treatment of Erectile Dysfunction, https:/pubmed.nobl.nlm.nih. gov/7752328/, Jun. 1995.

Kim, et al., Papaverine Topical Gel for Treatment of Erectile Dysfunction, ov/7815584/, Feb. 1995.

Pitzanti, et al., TRANSCUTOL @ P Containing SLNs for Improving 8-Methoxypsoralen Skin Delivery, Pharmaceutics 2020, Oct. 15, 2020, pp. 1-14.

International Search Report on related PCT Application No. PCT/US2021/056364 from International Searching Authority (KIPO) dated Feb. 15, 2022.

Written Opinion on related PCT Application No. PCT/US2021/056364 from International Searching Authority (KIPO) dated Feb. 15, 2022.

Krishan, Mansi et al., "Manipulation of olfactory tight junctions using papaverine to enhance intranasal delivery of gemcitabine to the brain", HHS Public Access Author Manuscript, Feb. 2014, 19 pages, Drug Deliv. Author manuscript.

Pharmacokinetics of Papaverine, Phentolamine, and Alprostadil, VerisimLife.

Berg et al., Variable Bioavailability of Papaverine, Pharmacol Toxicol, May 1988, https://pubmed.ncbi.nlm.nih.gov/3413033/ [Abstract Only].

Kraus et al., Pharmacokinetics and Bioavailability of Papaverine HCl Following Intravenous, Peroral, Rectal, Vaginal, Topical and Buccal Administration in Beagle Dogs, Biopharm Drug Dispos., Oct. 1991, https://pubmed.ncbi.nlm.nih.gov/1932615/ [Abstract Only].

Shaaya et al., Pharmacokinetics and Bioavailability of Papaverine HCl After Intravenous, Intracorporeal and Penis Topical Administration in Beagle Dogs, Methods Find Exp Clin Pharmacol. Jun. 1992, https://pubmed.ncbi.nlm.nih.gov/1513193/ [Abstract Only].

Australian Product Information—DBL™ Papaverine Hydrochloride Injection (Papaverine Hydrochloride), Pfizer Australia Pty Ltd., Oct. 8, 2991.

DBL™ Papaverine Hydrochloride, DBL™ Papaverine Hydrochloride Injection, Pfizer Australia Pty Ltd., May 2021.

Ritschel et al., Pharmacokinetics of Papaverine in Man, Int J Clin Pharmacol Biopharm, May 15, 1977, https://pubmed.ncbi.nlm.nih.gov/873666/ [Abstract Only].

Wen et al., Systemic Enhancement of Papaverine Transdermal Gel for Erectiledysfunction, Drug Dev Ind Pharm. Aug. 2012, https://pubmed.ncbi.nlm.nih.gov/22080854/ [Abstract Only].

Kan et al., UPLC-MS/MS Determination of Phentolamine in Human Plasma and Its Application to a Pharmacokinetic Study, Drug Res (Stuttg), Nov. 2014, https://pubmed.ncbi.nlm.nih.gov/24452521/ [Abstract Only].

Goldstein et al., Vasomax for the Treatment of Male Erectile Dysfunction, World J. Urol. Feb. 2001, https://pubmed.ncbi.nlm.nih.gov/11289671/ [Abstract Only].

Silva et al., Phentolamine Bioequivalence Study, Int J. Clin Pharmacol Ther., Jan. 2004, https://pubmed.ncbi.nlm.nih.gov/14756387/ [Abstract Only].

Cawello et al., Dose Proportional Pharmacokinetics of Alprostadil (Prostaglandin $E_1$) in Healthy Volunteers Following Intravenous Infusion, British Journal of Clinical Pharmacology, 1995, pp. 273-276.

Zhang et al., Determination of Prostaglandin $E_1$ in Dog Plasma Using Liquid Chromatography—Tandem Mass Spectroetry and Its Application to a Parmacokinetic Study, J Chromatogr B Analyt Technol Biomed Life Sic., Oct. 15, 2013, https://pubmed.ncbi.nlm.nih.gov/24029554/ [Abstract Only].

Lea et al., Intracavernous Alprostadil. A Review of Its Pharmacodynamic Andparmacokinetic Properties and Therapeutic Potential in Erectile Dysfunction, Drugs Aging, Jan. 1996, https://pubmed.ncbi.nlm.nih.gov/8785470/ [Abstract Only].

Cawella et al., Pharmacokinetics of Prostaglandin $E_1$ and Its Main Metabolites After Intracavernous Injection and Short-Term Infusion of Prostaglandin $E_1$ in Patients With Erectile Dysfunction, J Urol. Oct. 1997, https://pubmed.ncbi.nlm.nih.gov/9302131/ [Abstract Only].

Highlights of Prescribing Information, Pharmacia & Upjohn Co., Nov. 2017.

\* cited by examiner

TRANSDERMAL TREATMENT FOR ERECTILE DYSFUNCTION

CROSS-REFERENCE TO RELATED APPLICATIONS

The application claims the benefit of U.S. Provisional Application No. 63/104,158 which was filed on Oct. 22, 2020, the entirety of which is hereby incorporated by reference.

BACKGROUND

The present disclosure relates to the field of treatment of erectile dysfunction, and more particularly to a transdermal treatment for erectile dysfunction.

Erectile dysfunction (ED) may affect 30% to 50% of men aged 40 to 70 years. First line therapy for ED treatment includes oral phosphodiesterase-5 (PDE-5) inhibitors such as sildenafil. However, not all patients can tolerate PDE-5 inhibitor therapy. Other weakness of this therapeutic approach include inconvenience and delayed reaction time.

Alprostadil, also known as prostaglandin El, is an approved second-line treatment for erectile dysfunction. Intracavernous injection of alprostadil is useful for its vasodilating effect, which acts by relaxing the smooth muscle of the corpus cavernosum, hence increasing the diameter of the cavernous arteries leading to an erection.

Alprostadil can be used as an intraurethral suppository or medicated urethral system, but has shown to be less efficient in inducing cavernous smooth muscle relaxation and also has more side effects. Also, transurethral therapy is inconvenient and invasive.

Another option is using alprostadil in combination with other medications. The combination of papaverine, phentolamine, and alprostadil, known as "TriMix," is particularly effective when used for intracavernous injection as a treatment for erectile dysfunction. TriMix has been used for such treatments for nearly 30 years.

Alprostadil (injection) and phentolamine (injection, suppository) are both FDA approved drugs with demonstrated nonclinical safety. Papaverine has not been approved by the FDA. However, it has been widely used for many decades as an IV and IM therapy, for irrigation of vascular grafts during vascular surgery, and as a vasodilator when taken orally. Through this extensive real-world data, papaverine has been found to be a non-controversial, safe and effective tool for its activity as a vasodilator/spasmolytic that acts directly on smooth muscle, independently of nervous system activity.

TriMix solutions may include varying concentrations of papaverine HCL (10-50 mg/mL), phentolamine mesylate (1-2 mg/mL), and alprostadil/prostaglandin E1 (10-25 mcg/mL). Such solutions are prepared in water for injection. Injection volumes of 0.2 cc to 0.5 cc can be prescribed.

A problem with TriMix is that it is only available from pharmacies authorized to produce such mixtures. Also, formulation concentrations of the three ingredients and the prescribed injection volumes vary from patient to patient. A physician works together with the patient to determine a TriMix injection formula that is most effective for the individual patient. Another problem with TriMix is that intracavernosal therapy is inconvenient and invasive, as it generally requires self-injection by the patient, leading to patient discomfort and possible fibrosis.

Studies have been undertaken in an attempt to develop an effective transdermal therapy for ED. For example, a study of a topically-applied papaverine gel suggested a possible, but limited, benefit to some patients. A study of a topically-applied papaverine and alprostadil gel indicated some transdermal permeability, but only a limited vascular response that did not induce erection. Alprostadil topical cream has been developed for ED patients with mild-to-severe symptoms. However, such cream does not appear to be nearly as effective as intracavernosal injections of TriMix.

SUMMARY

The present disclosure discloses aspects that improve the solubility of each of the TriMix compounds, and also improve the skin permeability of each of the TriMix compounds when dissolved in a cream or other medium configured for topical application. For example, as expected, the solubility of Papaverine was improved by mixing it with an aqueous solution of selected excipients. Surprisingly, however, the solubility of papaverine was further improved when phentolamine and prostaglandin E1 were added to the solution. Also, a solution of prostaglandin E1 and selected excipients exhibited a level of permeability through skin. Surprisingly, however, when papaverine and phentolamine were added to the solution, the skin permeability of prostaglandin E1 was increased. This pattern was true for each of the other compounds. To wit, the skin permeability of papaverine increased when prostaglandin E1 and phentolamine were added, and the skin permeability of phentolamine was increased when prostaglandin E1 and papaverine were added. As such, a combination of paparavine, phentolamine, and prostaglandin E1 combined with selected excipients in a topical medium can be an effective transdermal treatment for erectile dysfunction, as pharmacologically effective amounts of such compounds can penetrate through the skin when the combination is applied to the penis.

In accordance with one embodiment, the present specification discloses a medical composition configured to be applied to a skin of a patient. The medical composition comprises a mixture of prostaglandin E1, phentolamine and papaverine HCl dissolved in a solvent solution comprising a plurality of excipients.

In some embodiments, the plurality of excipients comprise a pH 4 buffer, transcutol p, glycerol, and benzyl alcohol. In additional embodiments, the plurality of excipients additionally comprise propylene glycol. In further embodiments, the plurality of excipients additionally comprise ethanol.

The present specification also discloses a method of treating erectile dysfunction, comprising applying to the skin a composition comprising a therapeutically effective dose of prostaglandin E1, phentolamine and papaverine.

In some embodiments the prostaglandin E1, phentolamine and paparavine are dissolved in a single solvent system comprising a plurality of excipients. The solution can comprise a pH 4 buffer, transcutol P, glycerol, and benzyl alcohol. The solution can additional comprise propylene glycol and/or ethanol.

The present specification further discloses a method of increasing the solubility of prostaglandin E1, comprising mixing the prostaglandin E1 in a solvent solution and adding papaverine and phentolamine to the solvent solution.

The present specification still further discloses a method of increasing the skin permeability of prostaglandin E1, paparevine, and phentolamine, comprising combining the prostaglandin E1, paparevine and phentolamine together into a single composition having a topical media configured for application to skin.

The composition can comprise a solvent system comprising a plurality of excipients.

DESCRIPTION

As discussed in more detail below, it has been discovered that the solubility of papaverine in a solvent system can be increased by adding phentolamine mesylate and prostaglandin E1 to the solvent system. Similarly, the solubility of phentolamine in a solvent system can be increased by adding papaverine and prostaglandin E1 to the system. Further, the skin permability of prostaglandin E1 in a composition can be increased by adding papaverine and phentolamine to the composition; the skin permeability of papaverine in a composition can be increased by adding prostaglandin E1 and phentolamine to the composition; and the skin permeability of phentolamine mesylate in a composition can be increased by adding prostaglandin E1 and papaverine to the composition. Thus, a topical media composition comprising a mixture of prostaglandin E1, papaverine and phentolamine, when applied to a user's penis, can deliver sufficient concentrations of all three drugs to provide an effective treatment for erectile dysfunction.

Prostaglandin E1, also known as Alprostadil, Caverject, Muse, 745-65-3, PGE1, Edex, Prostin VR, Alprostadilum, and Femprox has a molecular weight of 354.5 g/mol. Its chemical formula is $C_{20}H_{34}O_5$, and its molecular structure is:

Phentolamine Mesylate, also known as Regitine, 50-60-2, Regitin, Fentolamin, Dibasin, Rogitine, Phentolaminum, Fentolamina, and C 7337 Ciba, has a molecular weight of 281.35 g/mol. Its chemical formula is $C_{17}H_{19}N_{30}$, and its molecular structure is:

Papaverine, also known as papaverine hydrochloride, 61-25-6, Cardiospan, Cardoverina, Papaversan, Forpavin, Papalease, Pavatest, Cerespan, Dispamil, Pavabid, Papacon, Para-Time SR, and Pavacot, has a molecular weight of 339.4 g/mol. Its chemical formula is $C_{20}H_{21}NO_4$, and its molecular structure is:

Prostaglandin E1, papaverine and phentolamine have been used for many years as an intracavernosal erectile dysfunction treatment known as TriMix.

It appears that none of the TriMix chemicals have particularly good skin permeability. However, it is known that combining a medication with excipients can sometimes improve skin permeability. But that which can be particularly effective in increasing skin permeability for one chemical can be ineffective, or even hinder, transdermal permeability for another chemical. And development of excipients to improve skin permeability for even one of the TriMix chemicals has proven difficult. Still further, each of these drugs displays very different solubilities, and interacts differently with different excipients. For example, papaverine is moderately soluble (about 2-3% w/w) in water, buffer solutions (pH 4 and 7) and glycerol, and poorly soluble in ethanol and transcutol P. Prostaglandin E1, however, is poorly soluble in water, buffer solutions (pH 4 and 7) and glycerol, and strongly soluble in ethanol and transcutol P. Yet further, each of the TriMix chemicals have differing properties concerning stability at particular temperatures and for particular lengths of time.

Aqueous solvent systems that could be incorporated into formulations suitable for topical application were developed and assessed for papaverine, phentolamine mesylate and prostaglandin E1 solubility (both individually and in combination). A target ratio of the three drugs was: papaverine HCl 5% w/w, phentolamine mesylate 1% w/w and prostaglandin E1 0.3% w/w. Solvent systems were developed with an aim to optimize drug thermodynamic activity (i.e., drugs incorporated at >=80% of the saturated solubility level). Three solvent systems (SSAG01, SSAG02 and SSAG04) (see Table 1 below) were developed and the saturated solubilities of the three drugs in the developed systems were assessed.

TABLE 1

Composition of solvent systems developed for papaverine HCl, phentolamine mesylate and prostaglandin E1

| | Composition (% w/w) of developed solvent systems | | |
|---|---|---|---|
| Excipient Name | SSAG01 | SSAG02 | SSAG04 |
| Ethanol | — | — | 5.00 |
| Citrate-phosphate pH 4 Buffer | 48.00 | 65.00 | 68.00 |

TABLE 1-continued

Composition of solvent systems developed for papaverine HCl, phentolamine mesylate and prostaglandin E1

| | Composition (% w/w) of developed solvent systems | | |
|---|---|---|---|
| Excipient Name | SSAG01 | SSAG02 | SSAG04 |
| Transcutol P | 25.00 | 18.00 | 15.00 |
| PEG 400 | 10.00 | — | — |
| Glycerol | 5.00 | 5.00 | 5.00 |
| Propylene Glycol | 10.00 | 10.00 | — |
| Benzyl alcohol | 2.00 | 2.00 | 2.00 |
| Total | 100.00 | 100.00 | 100.00 |

Table 2 (below) presents results of solubility studies of the drugs in the solvent systems. For each solvent system, the solubility of papaverine was evaluated when only papaverine was added to the solvent system, and the solubility of prostaglandin was evaluated when only prostaglandin was added to the solvent system. Also, the solubility of each drug was evaluated when a combination of all three drugs was added to each solvent system.

In comparison to drug solubility in individual excipients, a marked increase in saturated solubility (6.39-7.25% w/w) was observed when papaverine HCl was assessed individually in all solvent systems. Solubility further improved (7.58-9.44% w/w) upon addition of phentolamine mesylate and prostaglandin E1. Thus, a solvent system was able to enhance solubility, but addition of the other drugs further enhanced solubility well beyond the enhancement attributable to the solvent system.

When assessed individually, the saturated solubility of prostaglandin E1 in SSAG01 surpassed the target concentration of 0.3% w/w (0.61% w/w). Though the target concentration was not reached in SSAG02 and SSAG04 (0.2% w/w for both) for the individual drug, the presence of phentolamine mesylate and papaverine HCl increased prostaglandin E1 solubility to 0.57% w/w and 0.56% w/w in SSAG02 and SSAG04, respectively. Thus, addition of the other drugs enhanced solubility to greatly surpass the target concentration.

TABLE 2

Saturated solubility of the three drugs (both individually and in combination) in developed solvent systems

| | | | Saturated solubility (% w/w) | | |
|---|---|---|---|---|---|
| Drug Name | | Amount added | SSAG01 | SSAG02 | SSAG04 |
| Individually | Papaverine HCl | 10% w/w | 6.39 (6.34-6.44) | 7.21 (7.18-7.25) | 7.25 (7.20-7.28) |
| | Prostaglandin E1 | 1% w/w | 0.61 (0.60-0.63) | 0.20 (0.19-0.23) | 0.20 (0.17-0.23) |
| Combined | Papaverine HCl | 10% w/w | 7.58 (7.55-7.61) | 9.44 (9.35-9.52) | 9.41 (9.39-9.43) |
| | Phentolamine Mesylate | 5% w/w | 4.62 (4.59-4.65) | 4.36 (4.34-4.39) | 4.39 (4.37-4.42) |
| | Prostaglandin E1 | 1% w/w | 0.53 (0.53-0.53) | 0.57 (0.55-0.58) | 0.56 (0.56-0.56) |

Since the solubility of each individual drug was observed to increase in the presence of the other two drugs, the combination of all three drugs appears to have a synergistic effect on solubility. Results confirmed that the initial target drug ratio (papaverine HCl 5% w/w, phentolamine mesylate 1% w/w and prostaglandin E1 0.3% w/w) could approximately be achieved with each solvent system when the drugs were in combination. Accordingly, in vitro permeation testing (IVPT) was also performed using the solvent systems.

Figure 1:
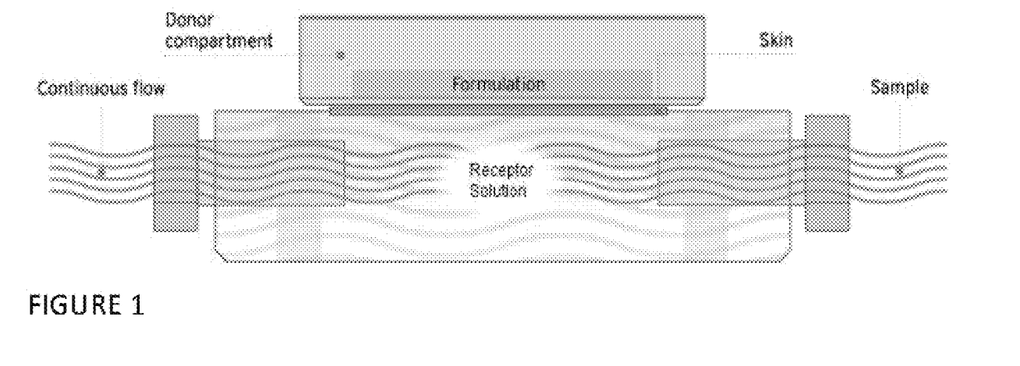
FIG. 1 is a schematic view of an embodiment of a diffusion cell designed to mimic the physiological and anatomical conditions of skin in situ.

With reference to FIG. 1, in vitro skin permeation experiments used a diffusion cell designed to mimic the physiological and anatomical conditions of skin in situ. The diffusion cell included a donor compartment configured to receive the formulation, or solvent system, to be tested. A receptor compartment included a flow path for receptor solution, which was to be analyzed. Dermatomed skin was arranged between the donor compartment and receptor compartment. As such, a formulation comprising the solvent system having the drug is applied to the skin in the donor compartment. A portion of the drug permeated through the skin into the receptor solution, which was analyzed to determine drug concentration at several time periods, including 0.25, 0.5, 1, 1.5 2, 4, 6 and 8 hours. Through testing, it was determined that all three compounds were acceptably stable in a receptor solution comprising a phosphate/citrate buffer (pH 4.0) with 0.01% Brij.

Epidermal sheet was prepared from a single human skin donor from cosmetic reduction surgery for use in the in vitro testing experiments. The subcutaneous fat was removed mechanically, and the skin was dermatomed to a thickness of 500±50 μm. Each cell used a 1 cm² sample of skin, and 1 mg of solution was applied to each skin sample during testing. Further information concerning the experiment is summarized in Table 3 below.

TABLE 3

Conditions for in vitro permeation testing (IVPT)

| Setup | Conditions |
|---|---|
| Skin type | Epidermal sheet (prepared from human abdominal skin from elective surgery) |
| No. skin donors | 1 |
| Receptor solution | Citrate/phosphate buffer pH 4.0 with 0.01% Brij |
| No. solvent systems | 6 |
| No. replicates | 5 |
| No. skin blanks | 1 |

TABLE 3-continued

Conditions for in vitro permeation testing (IVPT)

| Setup | Conditions |
|---|---|
| Target solvent system dose amount | 10 mg |
| Receptor solution flow rate | 6 uL/min |
| Receptor solution collection times | 0.25, 0.5, 1, 1.5, 2, 4, 6, 8 hr |

Each of the solvent systems (SSAG01, SSAG02, SSAG04) were tested with a combination of all drugs/compounds, and the receptor solution was analyzed to determine the amount of each compound that permeated through the skin. The SSAG02 solvent system was also individually tested with each of the compounds alone, and thus measurements were made to determine skin permeation for each drug when that drug alone was in the SSAG02 solvent system. Table 4 (below) presents data concerning the solvent systems and compounds tested with such solvent systems.

TABLE 4

Summary of solvent systems used in the in vitro permeation testing (IVPT)

| Solvent System | Figure Label | Active Compound | % w/w |
|---|---|---|---|
| SSAG01 | SSAG01 combo_Phento | Phentolamine | 10% |
|  | SSAG01 combo_Papav | Papaverine | 5% |
|  | SSAG01 combo_PGE1 | Prostaglandin E1 | 0.6% |
| SSAG02 | SSAG02 combo_Phento | Phentolamine | 10% |
|  | SSAG02 combo_Papav | Papaverine | 5% |
|  | SSAG02 combo_PGE1 | Prostaglandin E1 | 0.6% |
| SSAG04 | SSAG04 combo_Phento | Phentolamine | 10% |
|  | SSAG04 combo_Papav | Papaverine | 5% |
|  | SSAG04 combo_PGE1 | Prostaglandin E1 | 0.6% |
| SSAG02 | SSAG02 + Phento | Phentolamine | 10% |
| SSAG02 | SSAG02 + Papav | Papaverine | 5% |
| SSAG02 | SSAG02 + PGE1 | Prostaglandin E1 | 0.6% |

The receptor solution was collected and analyzed as discussed. The cumulative amount per cm² of phentolamine, papaverine, and prostaglandin permeated into the receptor solution was calculated from drug concentrations measured in the receptor solution over time. The cumulative amount per cm² of phentolamine, papaverine, and prostaglandin at the final timepoint was calculated for each replicate. The flux (ng/cm²/hr) of phentolamine, papaverine and prostaglandin E1 over time was also measured and calculated for each replicate. Means and standard errors were calculated and reported in figures and tables, including Tables 5 and 6 below.

TABLE 5

Mean cumulative amount of phentolamine, papaverine, and prostaglandin E1 (ng/cm²) delivered to the receptor solution 1 hr post-application for each solvent system

| | Mean cumulative amount of phentolamine, papaverine, and prostaglandin E1 (PGE1) (ng/cm²) | | | |
|---|---|---|---|---|
| Solvent System | N | Mean | Std Dev | Std Err |
| SSAG04 combo_Papav | 5 | 178105.86 | 218456.55 | 97696.74 |
| SSAG04 combo_PGE1 | 5 | 9591.80 | 11842.37 | 5296.07 |
| SSAG04 combo_Phento | 5 | 70727.71 | 85415.24 | 38198.86 |
| SSAG02 combo_Papav | 4 | 37022.06 | 72528.98 | 36264.49 |
| SSAG02 combo_PGE1 | 4 | 1920.36 | 3787.83 | 1893.92 |
| SSAG02 combo_Phento | 4 | 15204.29 | 29609.17 | 14804.59 |
| SSAG02 + Papav | 3 | 25142.44 | 24038.42 | 13878.59 |
| SSAG02 + PGE1 | 4 | 117.72 | 235.34 | 117.67 |
| SSAG02 + Phento | 4 | 10524.76 | 13240.06 | 6820.03 |

TABLE 5-continued

Mean cumulative amount of phentolamine, papaverine, and prostaglandin E1 (ng/cm$^2$) delivered to the receptor solution 1 hr post-application for each solvent system

| Solvent System | Mean cumulative amount of phentolamine, papaverine, and prostaglandin E1 (PGE1) (ng/cm$^2$) | | | |
|---|---|---|---|---|
| | N | Mean | Std Dev | Std Err |
| SSAG01 combo_Papav | 4 | 15.80 | 25.33 | 12.66 |
| SSAG01 combo_PGE1 | 4 | 0.66 | 1.00 | 0.50 |
| SSAG01 combo_Phento | 4 | 12.67 | 20.67 | 10.33 |

TABLE 6

Mean flux dose of phentolamine, papaverine and prostaglandin E1 (ng/cm$^2$/hr) delivered to the receptor solution 1 hr post-application for each solvent system

| Solvent System | Mean flux of phentolamine, papaverine, and prostaglandin E1 (PGE1) (ng/cm$^2$/hr) | | | |
|---|---|---|---|---|
| | N | Mean | Std Dev | Std Err |
| SSAG04 combo_Papav | 5 | 132840.00 | 193865.26 | 86699.18 |
| SSAG04 combo_PGE1 | 5 | 7848.07 | 11382.06 | 5090.21 |
| SSAG04 combo_Phento | 5 | 52617.66 | 75002.41 | 33542.10 |
| SSAG02 combo_Papav | 4 | 34881.96 | 67957.49 | 33978.74 |
| SSAG02 combo_PGE1 | 4 | 1725.52 | 3385.97 | 1692.99 |
| SSAG02 combo_Phento | 4 | 14021.56 | 27139.91 | 13569.95 |
| SSAG02 + Papav | 3 | 9747.13 | 8822.48 | 5093.66 |
| SSAG02 + PGE1 | 4 | 115.25 | 230.37 | 115.18 |
| SSAG02 + Phento | 4 | 7045.20 | 5472.00 | 2736.00 |
| SSAG01 combo_Papav | 4 | 23.12 | 36.98 | 18.49 |
| SSAG01 combo_PGE1 | 4 | 1.10 | 1.66 | 0.83 |
| SSAG01 combo _Phento | 4 | 20.51 | 33.63 | 16.82 |

Figure 2:
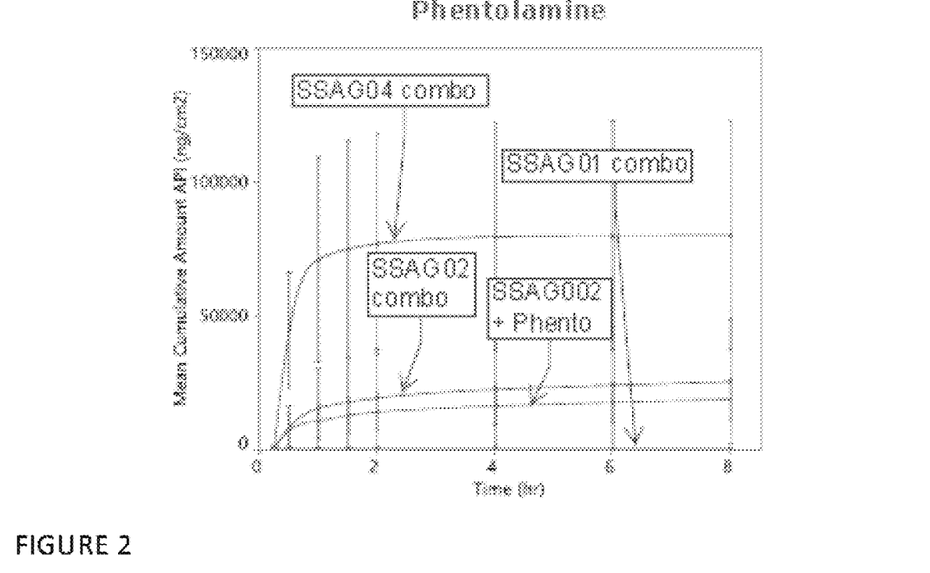
FIG. 2 is a graph showing the mean cumulative amount of phentolamine delivered to the receptor solution for each of four solvent systems.

With reference next to FIG. 2, the cumulative amount of phentolamine detected in the receptor solution is plotted versus time for each of the tested solvent systems, including each solvent system having a combination of all of the drugs and the SSAG02 solvent system having only phentolamine. Notably, a much greater amount of phentolamine permeated through the skin for the solvent system of SSAG02 with all of the drugs than did for the SSAG02 solvent system having only phentolamine.

Figure 3:
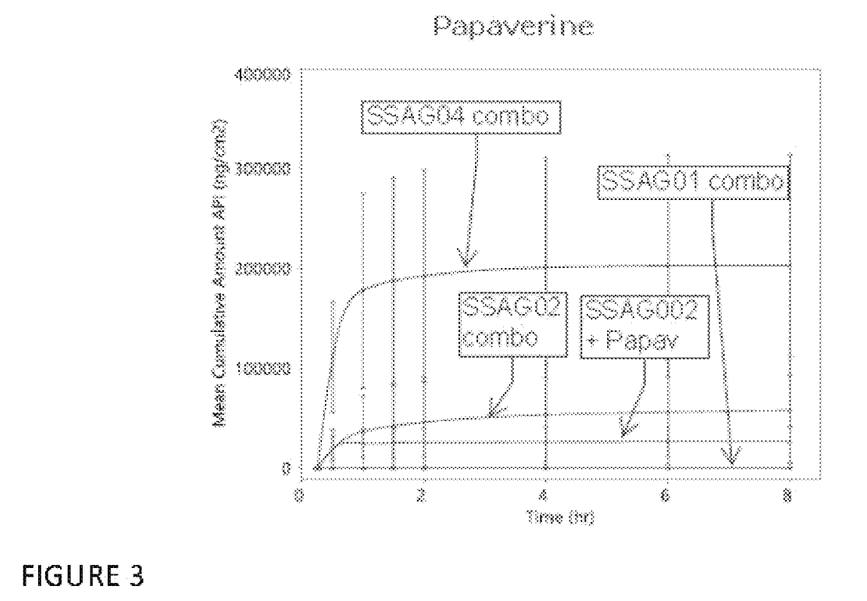
FIG. 3 is a graph showing the mean cumulative amount of papaverine delivered to the receptor solution for each of four solvent systems.

Similarly, with reference to FIG. 3, the cumulative amount of papaverine detected in the receptor solution is plotted versus time for each of the tested solvent systems, including each solvent system having a combination of all of the drugs and the SSAG02 solvent system having only papaverine. Notably, a much greater amount of papaverine permeated through the skin for the solvent system of SSAG02 with all of the drugs than did for the SSAG02 solvent system having only papaverine.

Figure 4:
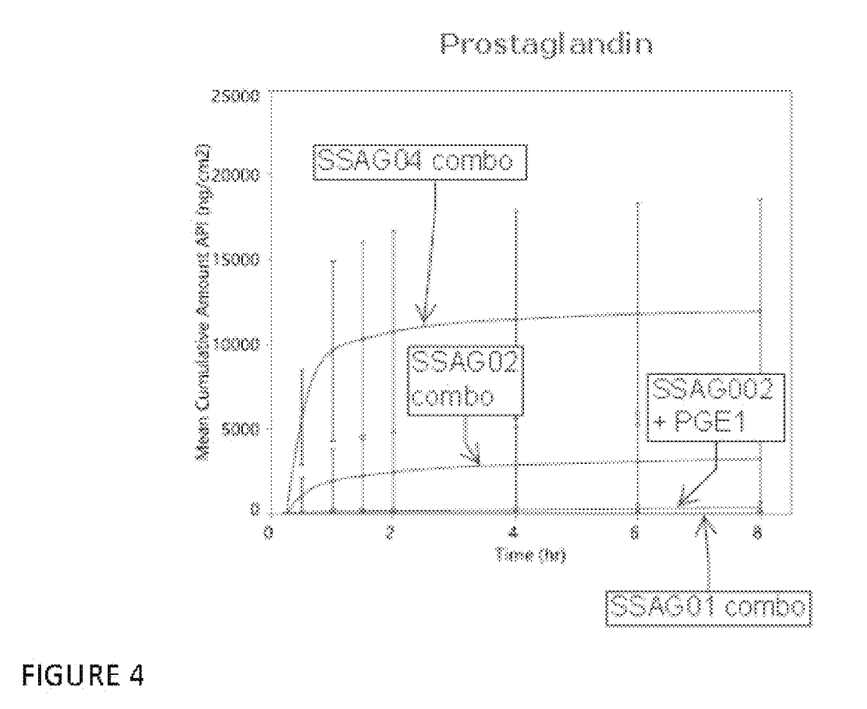
FIG. 4 is a graph showing the mean cumulative amount of prostaglandin E1 delivered to the receptor solution for each of four solvent systems.

Also, with reference to FIG. 4, the cumulative amount of prostaglandin detected in the receptor solution is plotted versus time for each of the tested solvent systems, including each solvent system having a combination of all of the drugs and the SSAG02 solvent system having only prostaglandin. Notably, a much greater amount of prostaglandin permeated through the skin for the solvent system of SSAG02 with all of the drugs than did for the SSAG02 solvent system having only prostaglandin.

Figure 5:
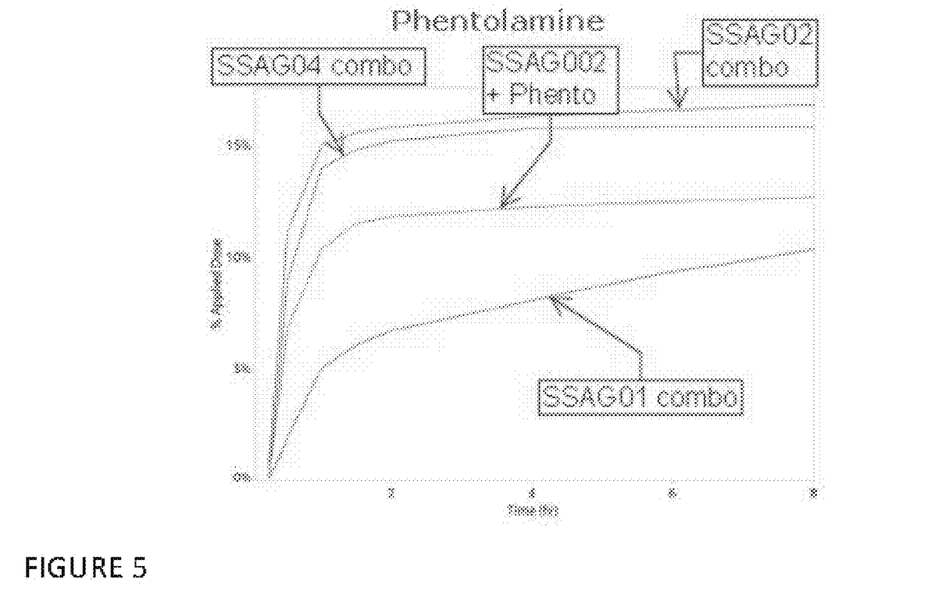
FIG. 5 is a graph showing the mean percent applied dose of phentolamine delivered to the receptor solution for each of four solvent systems.
Figure 6:
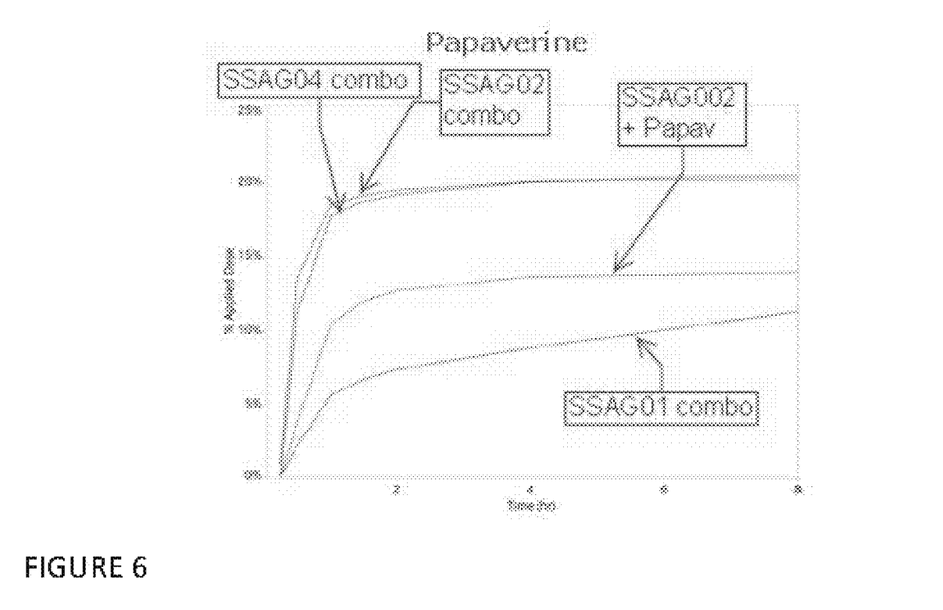
FIG. 6 is a graph showing the mean percent applied dose of papaverine delivered to the receptor solution for each of four solvent systems.
Figure 7:
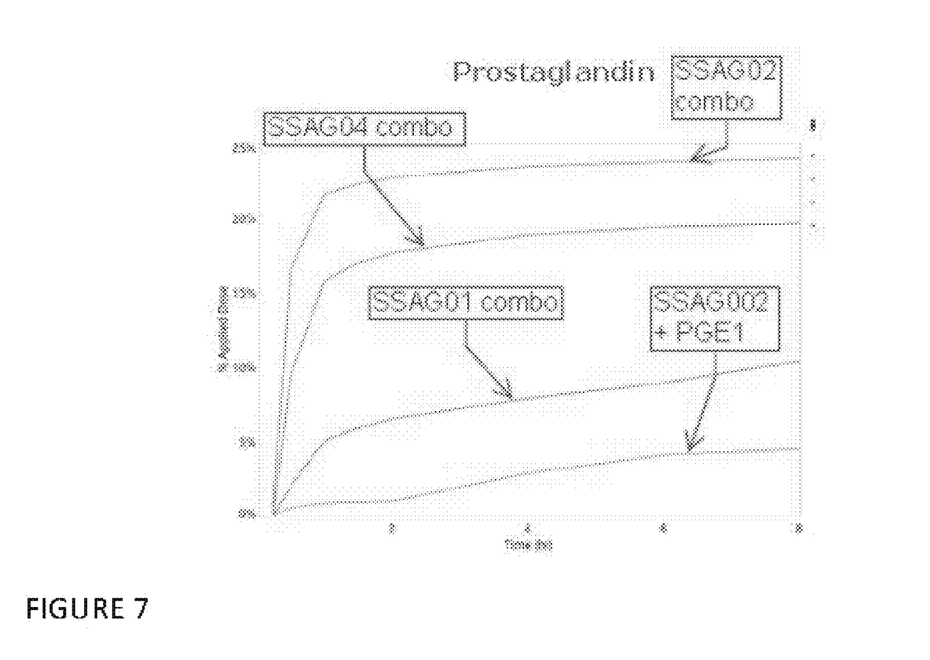
FIG. 7 is a graph showing the mean percent applied dose of prostaglandin E1 delivered to the receptor solution for each of four solvent systems.
Figure 8:
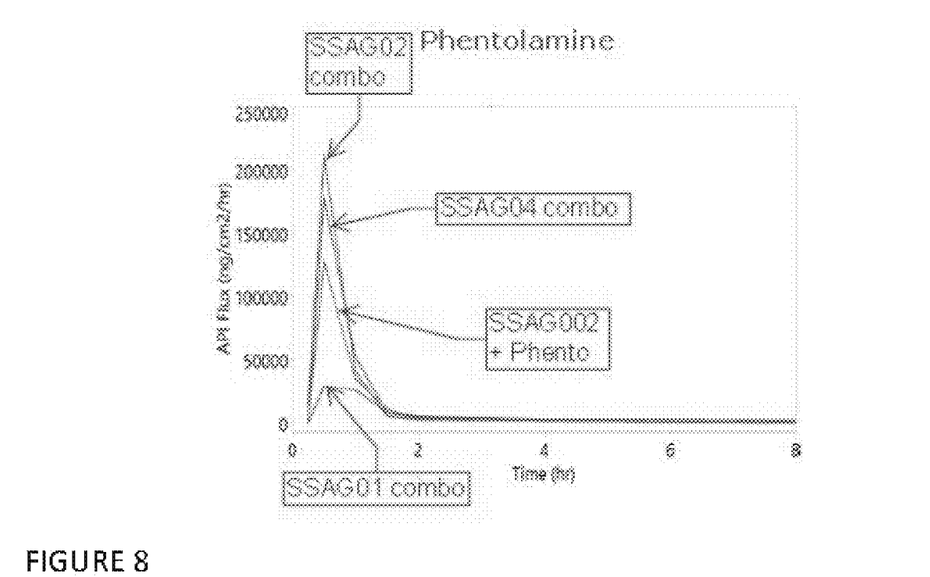
FIG. 8 is a graph showing the mean flux dose of phentolamine delivered to the receptor solution for each of four solvent systems.
Figure 9:
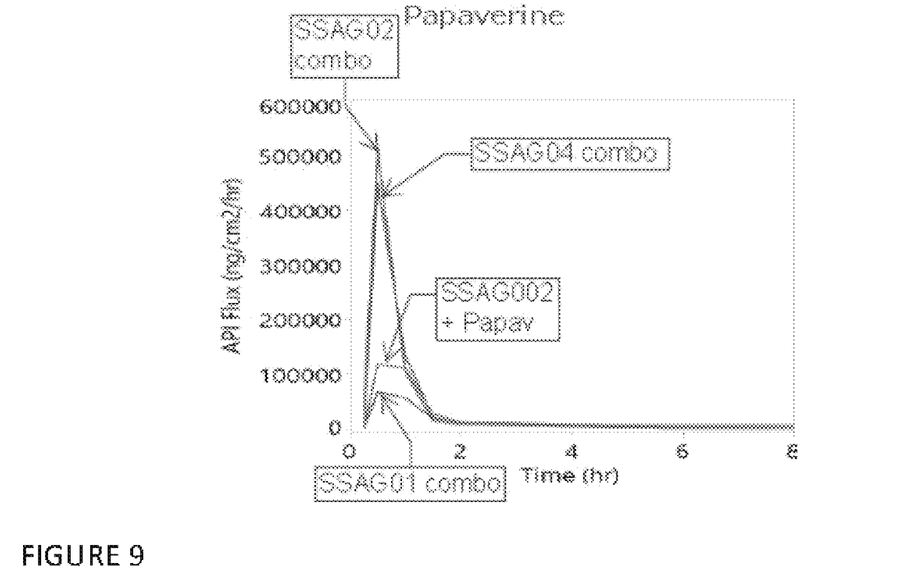
FIG. 9 is a graph showing the mean flux dose of papaverine delivered to the receptor solution for each of four solvent systems.
Figure 10:
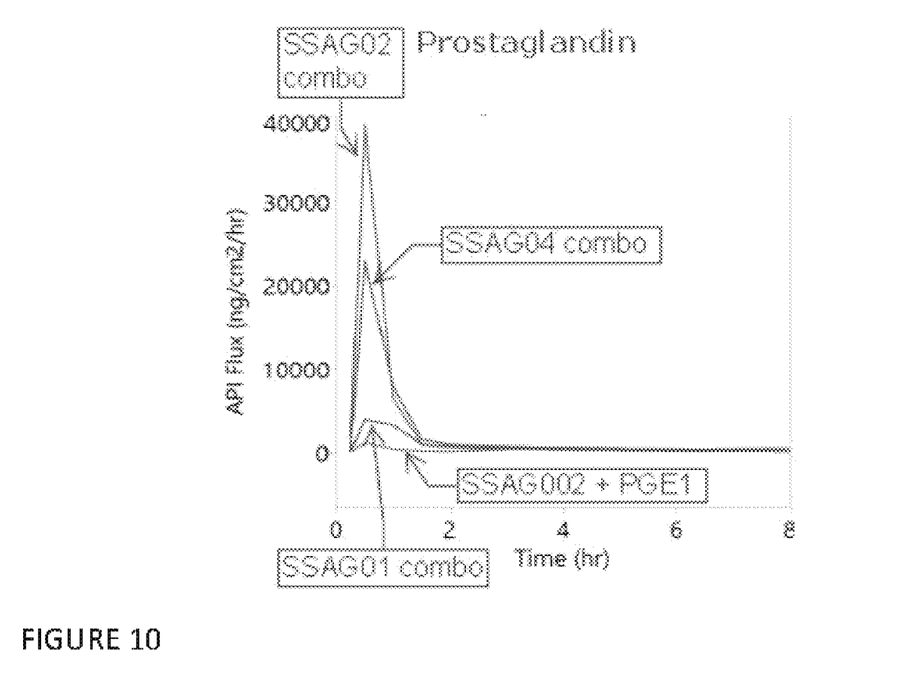
FIG. 10 is a graph showing the mean flux dose of prostaglandin E1 delivered to the receptor solution for each of four solvent systems.

FIGS. 5-7 show the applied dose of phentolamine, papaverine and prostaglandin, respectively, over time with each of the solvent systems as presented in FIGS. 2-4, and FIGS. 8-10 show the flux of phentolamine, papaverine and prostaglandin, respectively, over time with each of the solvent systems as presented in FIGS. 2-4.

As demonstrated in the Tables and Figures, all three drugs permeate rapidly through human epidermal sheet into the receptor solution, with most of the permeation taking place over the first hour. The solvent system composition had a major effect on permeation, with SSAG04 delivering higher amounts of each of the three drugs to the receptor solution, followed by SSAG02 and SSAG01. Comparison of the results for the individual solvent systems dissolved in SSAG02 with the results for the SSAG02 having a combination of all drugs shows that the SSAG02 combination solvent system delivered higher amounts of all three drugs to the receptor solution compared to the SSAG02 with individual drugs, indicating a synergistic relationship between phentolamine, papaverine, and prostaglandin when applied in combination (e.g. eutectic or pairing etc.). This is similar to the synergistic effect observed in terms of solubility, as discussed above, with improved solubility being observed with all 3 drugs in combination versus individual solubility values.

A fast onset of action is highly sought after in the treatment of erectile dysfunction. Since all three drugs permeated rapidly through human epidermal sheet into the receptor solution, with most of the permeation taking place over the first hour, medical compositions having a combination of all three drugs, which take advantage of the unexpected synergy in connection with skin permeability, lend themselves to a transdermal treatment for erectile dysfunction. Such a medical composition would include papaverine, phentolamine and prostaglandin E1, preferably included in solvent solution that is part of a topical media such as a cream or gel. The medical composition can be applied to the skin of a user's penis. The drugs will permeate through the skin and act directly on the tissues of the penis, leading to an erection as does intracavernosal injection of TriMix.

The discussion above has disclosed certain experimental results and factors with substantial specificity. This has provided a good context for disclosing and discussing inventive subject matter. However, it is to be understood that other embodiments may employ different specific features and interactions, such as different excipients at different concentrations, as well as different concentrations of papaverine, phentolamine and prostaglandin E1.

Although inventive subject matter has been disclosed in the context of certain preferred or illustrated embodiments and examples, it will be understood by those skilled in the art that the inventive subject matter extends beyond the specifically disclosed embodiments to other alternative embodiments and/or uses of the invention and obvious modifications and equivalents thereof. As such, modifications, which are within the scope of the inventive subject matter, will be readily apparent to those of skill in the art based upon this disclosure. It is also contemplated that various combinations or subcombinations of the specific features and aspects of the disclosed embodiments may be made and still fall within the scope of the inventive subject matter. Accordingly, it should be understood that various features and aspects of the disclosed embodiments can be combined with or substituted for one another in order to form varying modes of the disclosed inventive subject matter. Thus, it is intended that the scope of the inventive subject matter herein disclosed should not be limited by the particular disclosed embodiments described above, but should be determined only by a fair reading of the claims that follow.

What is claimed is:

1. A method of increasing the solubility of prostaglandin E1 that has been mixed with a solvent system configured for topical application to skin, the solvent system comprising PEG 400, comprising adding papaverine and phentolamine to the solvent system.

2. A method of increasing the skin permeability of each of prostaglandin E1 that has been mixed with a topical media configured for application to skin, the topical media comprising PEG 400, papaverine that has been mixed with the topical media comprising PEG 400, and phentolamine that has been mixed with the topical media comprising PEG 400, comprising combining the prostaglandin E1, papaverine and phentolamine together into a single composition having the topical media comprising PEG 400.

3. The method of claim 2, wherein the composition comprises a solvent system comprising a plurality of excipients.

4. The method of claim 2, wherein the topical media comprises a pH 4 buffer and transcutol p.

5. The method of claim 2, wherein the topical media additionally comprises propylene glycol.

6. The method of claim 5, wherein the topical media does not include ethanol.

7. The method of claim 1, wherein the solvent system comprises transcutol P.

8. The method of claim 7, wherein the solvent system additionally comprises propylene glycol.

9. The method of claim 7, wherein the solvent system does not include ethanol.

10. The method of claim 1, wherein the only active pharmaceutical ingredients mixed in the solvent system are the prostaglandin E1, papaverine and phentolamine.

* * * * *